(12) United States Patent
Greathouse

(10) Patent No.: US 7,502,500 B2
(45) Date of Patent: Mar. 10, 2009

(54) AUTOMATED PROCESSING OF DYNAMIC CARDIAC ACQUISITION DATA

(75) Inventor: William G. Greathouse, Brecksville, OH (US)

(73) Assignee: GVI Technology Partners, Ltd., Twinsburg, OH (US)

( * ) Notice: Subject to any disclaimer, the term of this patent is extended or adjusted under 35 U.S.C. 154(b) by 660 days.

(21) Appl. No.: 11/241,686

(22) Filed: Sep. 30, 2005

(65) Prior Publication Data

US 2006/0074306 A1      Apr. 6, 2006

Related U.S. Application Data

(60) Provisional application No. 60/614,796, filed on Sep. 30, 2004.

(51) Int. Cl.
*G06K 9/00* (2006.01)
*A61B 6/00* (2006.01)

(52) U.S. Cl. .................................. 382/128; 600/431
(58) Field of Classification Search ......... 382/128–134, 382/154, 173, 237; 378/98.2, 98.8, 4, 8; 128/922, 920; 600/407, 425–429, 410, 454, 600/436, 437; 345/204, 419, 427; 377/10; 356/12, 37
See application file for complete search history.

(56) References Cited

U.S. PATENT DOCUMENTS

| 4,151,416 | A | 4/1979 | Richey et al. |
|---|---|---|---|
| 4,223,221 | A | 9/1980 | Gambini et al. |
| 4,424,446 | A | 1/1984 | Inbar et al. |
| 4,882,494 | A | 11/1989 | Rogers et al. |
| 4,899,054 | A | 2/1990 | Barfod |
| 5,079,424 | A | 1/1992 | Kobayashi |
| 5,171,986 | A | 12/1992 | Loomis et al. |
| 5,237,173 | A | 8/1993 | Stark et al. |
| 5,412,215 | A | 5/1995 | Shuto et al. |
| 5,550,377 | A | 8/1996 | Petrillo et al. |
| 5,646,408 | A | 7/1997 | Goldberg et al. |
| 5,677,536 | A | 10/1997 | Vickers |
| 6,087,656 | A | 7/2000 | Kimmich et al. |
| 6,134,293 | A | 10/2000 | Guendel |
| 6,342,698 | B1 | 1/2002 | Stark |
| 6,757,423 | B1 * | 6/2004 | Amini .................. 382/154 |
| 7,158,661 | B2 * | 1/2007 | Inoue .................. 382/128 |
| 7,346,381 | B2 * | 3/2008 | Okerlund et al. ......... 600/407 |
| 2002/0163996 | A1 | 11/2002 | Kerrien et al. |
| 2003/0057375 | A1 | 3/2003 | Williams et al. |

OTHER PUBLICATIONS

International Search Report dated Jun. 26, 2006.

* cited by examiner

*Primary Examiner*—Samir A Ahmed
*Assistant Examiner*—Mehdi Rashidian
(74) *Attorney, Agent, or Firm*—Pearne & Gordon LLP

(57) ABSTRACT

Provided is a system and method for acquiring and processing dynamic cardiac data, comprising a radiation detector for acquiring image data, identifying a region of interest by performing, for example, a weighted center of mass calculation, generating an activity versus time array corresponding to the region of interest, and analyzing the activity versus time array for compactness and/or fragmentation by performing, for example, a full width half maximum calculation.

25 Claims, 10 Drawing Sheets

(8 of 10 Drawing Sheet(s) Filed in Color)

AUTOMATED PROCESSING OF DYNAMIC CARDIAC ACQUISITION DATA

CROSS-REFERENCES TO RELATED APPLICATIONS

This application claims the benefit of the following provisional application: 60/614,796 filed on Sep. 30, 2004, herein incorporated by reference in its entirety.

The disclosure of this patent document contains material, which is subject to copyright protection, specifically the Computer Program Listing of the appendix. The copyright owner has no objection to the facsimile reproduction by anyone of the patent document or the patent disclosure, as required by law or the United States patent Office, but otherwise reserves all copyright rights whatsoever.

REFERENCE TO COMPUTER PROGRAM LISTING

A computer program listing is included as an appendix attached to this disclosure in the form of two identical compact discs labeled COPY 1 and COPY 2 respectively, created on Sep. 29, 2005, in MS-Windows format compatible with an IBM PC compatible machine, each containing the computer program module listed below, said module in ASCII text format, with sizes and creation dates as listed below:

Name: SourceCode-2.txt Size: 26,502 Bytes Created: Sep. 29, 2004

The computer program listing appendix is incorporated by reference, in its entirety, into this specification.

FIELD OF THE INVENTION

This application relates generally to an apparatus and method for image analysis.

More specifically, this application relates to an apparatus and method for automated processing of dynamic cardiac acquisition data, with qualitative quantitative analysis, wherein the data can be acquired by a nuclear medicine imaging system.

BACKGROUND OF THE INVENTION

In the field of Medical Imaging, one modality is nuclear medicine (gamma camera) imaging. This uses a detector consisting of a scintillator backed by a plurality of photomultiplier tubes (PMTs) with appropriate electronics. A patient is given a radioisotope either by injection or ingestion and the detector(s), after being placed in close proximity to the patient, can determine where the radioisotope goes or has gone.

When the radioisotope emits a gamma photon in the direction of the detector, it is absorbed by the scintillator. The scintillator emits a flash of light (a scintila) which is detected by one or more of the plurality of PMTs. The PMTs nearest to the flash typically receive a stronger signal than those further away. By measuring the intensity of the flash at each PMT, then performing a calculation, for example a centroid type calculation, a fairly accurate estimation of where the flash occurred is possible.

The output of each of the PMTs is an electrical current proportional to the amount of light detected by the PMT. The PMT output current can be converted into a voltage and amplified and then integrated to derive the total energy (light) detected by each PMT.

Gamma camera systems and methods that can be used with the disclosed invention are described in co-pending U.S. patent applications Ser. No. 11/101,673 filed on Apr. 8, 2005; Ser. No. 11/140,337 filed on May 27, 2005; Ser. No. 11/140,336 filed on May 27, 2005; and Ser. No. 11/171,028 filed on Jun. 30, 2005; and provisional application Ser. No. 60/615,831, filed on Oct. 4, 2004; each incorporated herein by reference for all that they teach.

In nuclear medicine cardiac first pass imaging, dynamic time varying data may be acquired during the first transit of the bolus of an injected radiotracer through the central circulatory system. The planar position of each data event may be recorded with embedded time information or the data may be accumulated into arrays of fixed or varying time. FIG. 1 shows a configuration in which a gamma detector is placed over the chest for imaging use. After the data is acquired and stored, it may be processed within a computer system to provide additional qualitative and quantitative information that may be viewed on a computer system, saved on a storage media for future viewing, and/or captured to an output device for offline viewing. The processing of the data may require a high degree of operator knowledge, skill, and training to provide reproducible and consistent results, and utilize an operator's time that could otherwise be spent elsewhere. Inter- and intra-operator variability may exist so that subsequent data collections and processing provide inconsistent results. Accordingly, a process and device that reduces operator interaction would be beneficial.

SUMMARY OF THE INVENTION

Provided is a method of processing patient data using a radiation detector and a computer, the method comprising the steps of:

acquiring image data representing an image, the acquiring performed for some period of time using the radiation detector;

detecting and isolating a feature portion of the image;

identifying at least one region of interest of the image based on the feature portion;

generating an activity versus time array corresponding to the at least one region of interest from the image data; and analyzing the activity versus time array for generating an output for use by a user.

Also provided is the above method where one or more of the steps are implemented by software running on a computer.

Further provided is a method of a processing patient data using a radiation detector and a computer, the method comprising the steps of:

acquiring image data representing an image, the acquiring performed for some period of time using the radiation detector;

using the computer for automatically detecting and isolating a feature portion of the image;

using the computer for automatically identifying at least one region of interest of the image based on the feature portion;

generating an activity versus time array corresponding to the at least one region of interest from the image data; and using the computer for automatically analyzing the activity versus time array for compactness and/or fragmentation.

Also provided is a system or apparatus for implementing one or more of the above methods.

Further provided is a system for acquiring and processing dynamic cardiac data, comprising: a radiation detector for acquiring image data representing an image from a patient for some period of time; and a computer.

The computer of the above system comprising: a storage medium for storing the image data; a processor; and a program memory for storing one or more programs for executing on the processor.

The one or more programs are capable of performing the steps of:

identifying a region of interest of an image represented by the image data, detecting and isolating a feature portion of the image, identifying at least one region of interest of the image based on the feature portion, generating an activity versus time array corresponding to the at least one region of interest from the image data, and analyzing the activity versus time array for compactness and/or fragmentation, An output device is also provided in the above system for outputting a result of the analyzing.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and other features and advantages of the present invention will become apparent to those skilled in the art to which the present invention relates upon reading the following description with reference to the accompanying drawings, in which.

DETAILED DESCRIPTION OF THE PREFERRED EMBODIMENTS

Provided is a method of automatically processing dynamic cardiac data, in at least one embodiment comprising the steps of acquiring a data set with a gamma camera, identifying a region of interest by performing a weighted center of mass calculation, generating an activity versus time array corresponding to the region of interest, and analyzing the activity versus time array for compactness by performing a full width half maximum calculation.

The methods as described above and hereinbelow can be performed by software running on a general purpose computer or a special purpose computer, in numerous manners as known in the art of computer software design. For example, a Microsoft Windows-based IBM compatible computer having storage capability, a processor, and program memory for running a compiled C program. Other example platforms include Linux machines, Macintosh computers, or any other programmable computer.

Further provided is a system for acquiring and processing dynamic cardiac data, comprising a radiation detector such as a gamma camera which includes means for acquiring a data set, means for identifying a region of interest by performing a weighted center of mass calculation, means for generating an activity versus time array corresponding to the region of interest, and means for analyzing the activity versus time array for compactness by performing a full width half maximum calculation.

Figure 1:
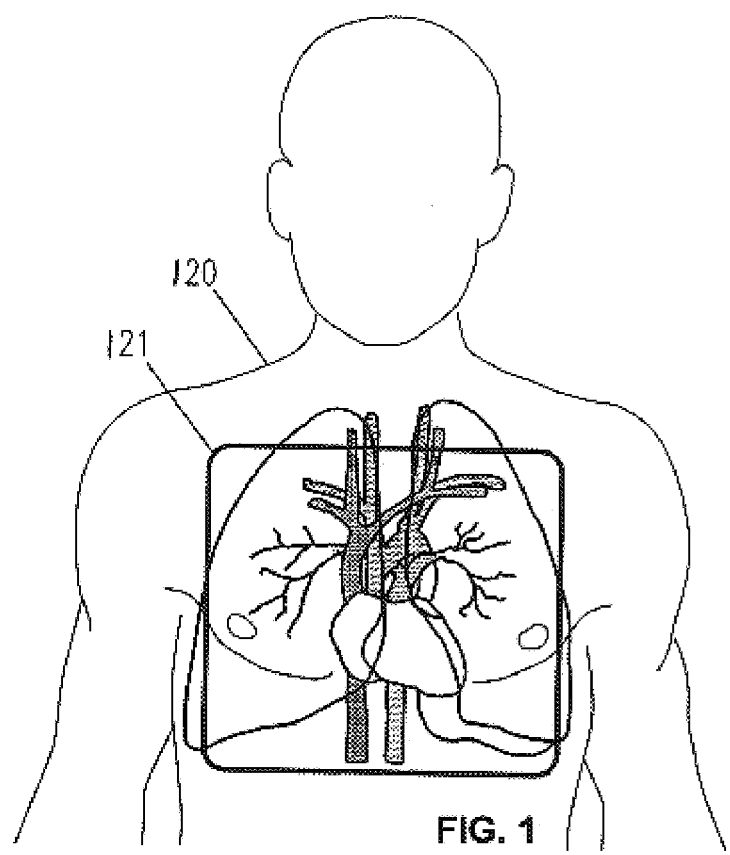
FIG. 1 shows a gamma detector imaging field of view for a cardiac monitoring system.
Figure 2:
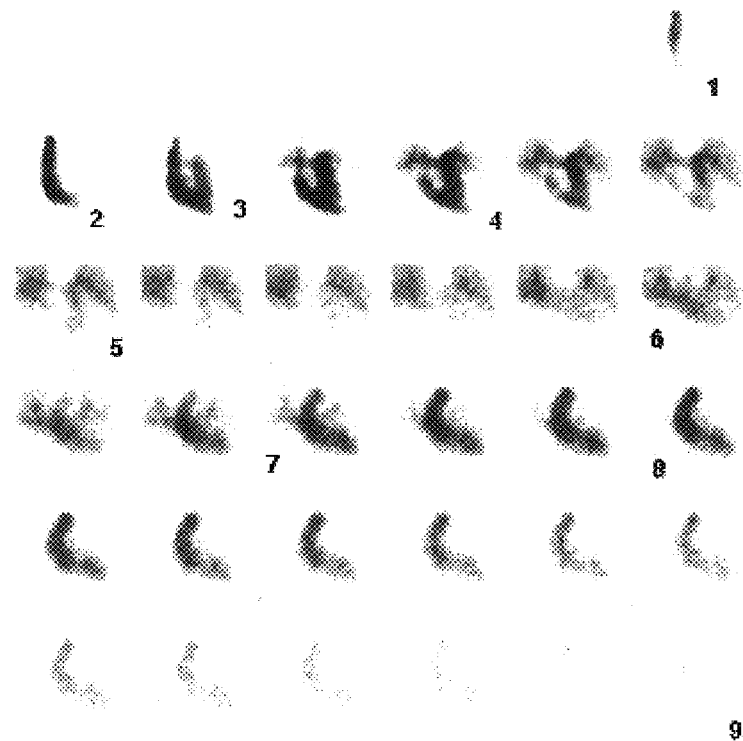
FIG. 2 shows a normal flow sequence through a cardiac system.

One or more embodiments of a system and method for automated processing of dynamic cardiac acquisition data with qualitative and quantitative analysis are described below with reference to the figures:

FIG. 1 shows a configuration in which a gamma detector is placed over the chest of a patient 120 with a field of view 121 that encompasses the central circulatory system, (including the superior vena cava, aorta, and pulmonary artery), heart, and lungs, for example. The position and angle of the detector may be varied to obtain a desired view of the bolus transit. Data may be acquired and stored for automated, or on demand, qualitative and quantitative processing and review. As illustrated in FIG. 2, the flow sequence is normally venous 5 to right atrium 6, right ventricle 7, and pulmonary artery 8. The flow then progresses through the lungs 9, left atrium 10, left ventricle 11, systemic arterial vasculature 12, and finally back to the venous side 13.

Figure 3:
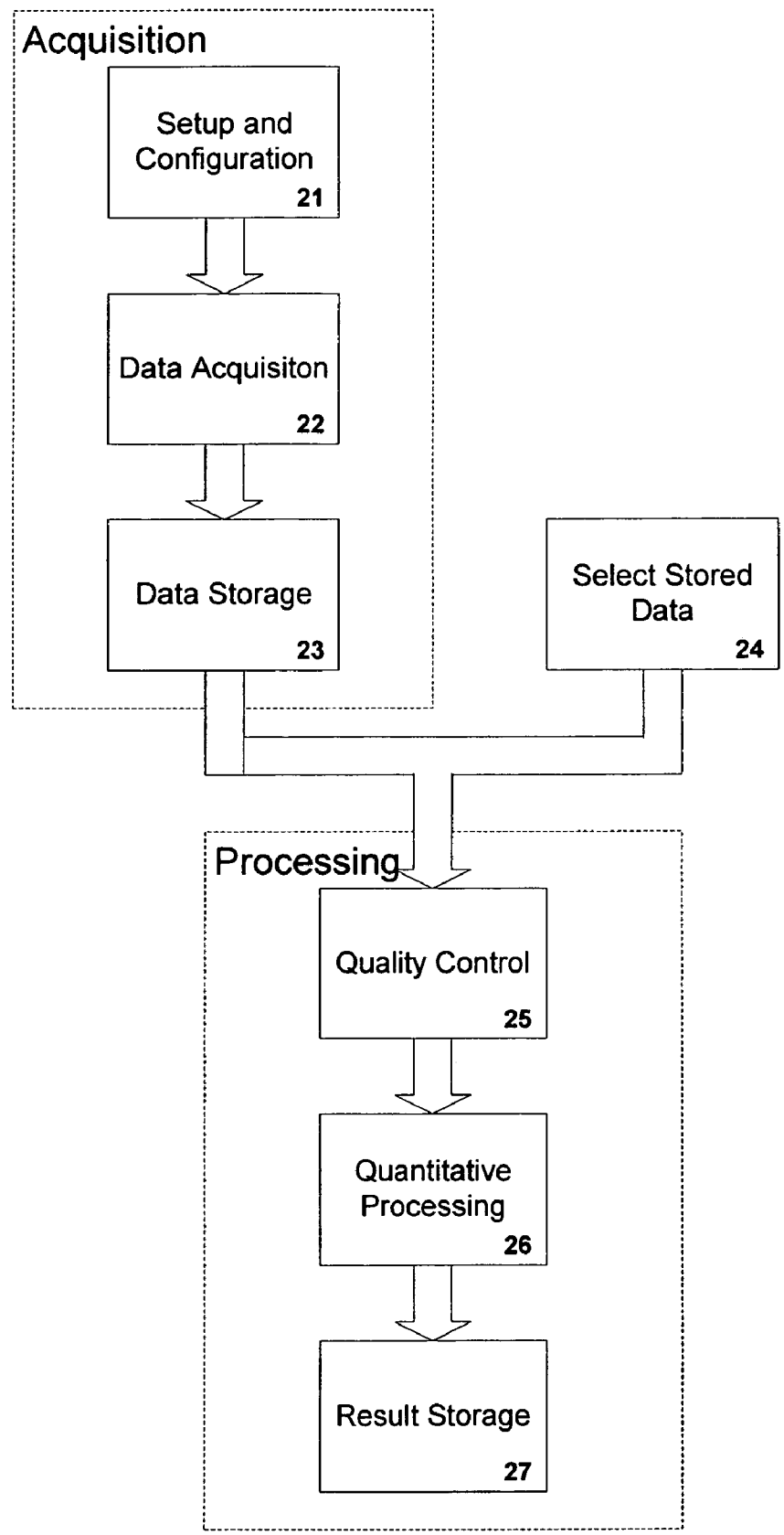
FIG. 3 is a function block diagram of a system for automated processing of dynamic cardiac acquisition data with quantitative analysis.

A function block diagram of a method of one embodiment for automated processing of dynamic cardiac acquisition data with quantitative analysis is provided in FIG. 3. After setup and configuration 21, acquisition 22 and storage 23 of the transit data, the processing phase may be entered automatically after acquisition by preloading the transit data or, alternatively, previously acquired and stored data 24 may be selected for processing. The processing and analysis of the data is divided into 3 phases: Quality Control 25, Quantitative Processing 26, and Storage 27.

The computer program listing appendix contains a partial source code for implementing a portion of the method according to a current embodiment of the invention, and is hereby incorporate by reference for all that it teaches, including the process implemented upon its execution by a computer. The source code is written in the C language and can be executed on a general purpose or dedicated computer for which it is compiled.

The user may interact with the application, for example, through an appropriate computer graphical user interface. Text, image, video, sound, and other data outputs can be displayed on one or more graphical monitors, can be printed out or graphics and/or video files saved or transmitted to another location or transferred to CD ROM or DVD ROM, for example. Input from the user may come from various input devices such as a mouse, keyboard, touch screen, tablet, or other input devices as appropriate to the task. The graphical user interface may be implemented using a custom display system or may, as an example, be provided by a Windows or X/Motif based computer system, for example.

Acquisition

Acquisition setup and configuration 21, for the current embodiment, consists of entering appropriate study information to associate the data with a particular patient and study, and any additional information as required to uniquely identify the acquired data. Typically, the study information contains, for example, patient name, patient height, patient weight, patient identification number, study identification number, series identification number, study description, technologist identification, physician identification, and comments. Other information may also be included or some of the listed information not included. Some or all of the information may be filled in automatically by the software system from stored or automatically generated data. The time interval for the acquisition, typically about 30 seconds, may be adjusted for the conditions of the current study. For a list mode acquisition, the time marker interval, typically about 1 ms, may be set. For fast frame mode acquisition, the frame interval, typically about 40 ms for a rest study and about 25 ms for a stress study, and the frame matrix, typically about 32×32 pixels, for example, may be set. The time interval and frame mode may be selected automatically by the software from stored data or calculated based on the other entered information, such as study type.

Data acquisition 22 of the current embodiment is performed based on the information entered during setup. The start point of the acquisition may be controlled automatically or manually and is selected so as to have an interval of steady state data before the appearance of the bolus in the field of view and to subsequently acquire all events associated with the passage of the bolus through the central circulatory system. List mode data sequentially records the X and Y location of each event with time marker values inserted in the sequential data to represent each time interval. Fast frame mode data is stored in a matrix of a predefined or selected size with each event occurrence incrementing the value stored at the X and Y location representative of the event location and at each time interval a new matrix is initialized for storing the data.

When the acquisition is complete, data storage 23 in the current embodiment is performed to make the data available for additional and future processing. The setup and configuration information and acquired data is stored to permanent storage, such as a hard disk drive file or database. This stored acquisition data or a different set of stored acquisition data may be selected 24 for further processing. Alternatively, data may be stored continuously or incrementally during the acquisition process.

Quality Control

The Quality Control 25 phase of processing in the current embodiment determines the ability for multiple and different operators to obtain reliable and repeatable results from the acquired data using both the automated processing method as described and manual processing methods. Several internal and external factors may affect the overall quality and integrity of the data. Some, but not all, of the factors that may affect the data quality include injection site selection, injection technique, bolus delivery, circulatory abnormalities, patient positioning, patient motion, and unrelated detected radioisotopes. The described method applies analytical methods to supplement operator knowledge requirements.

Figure 4:
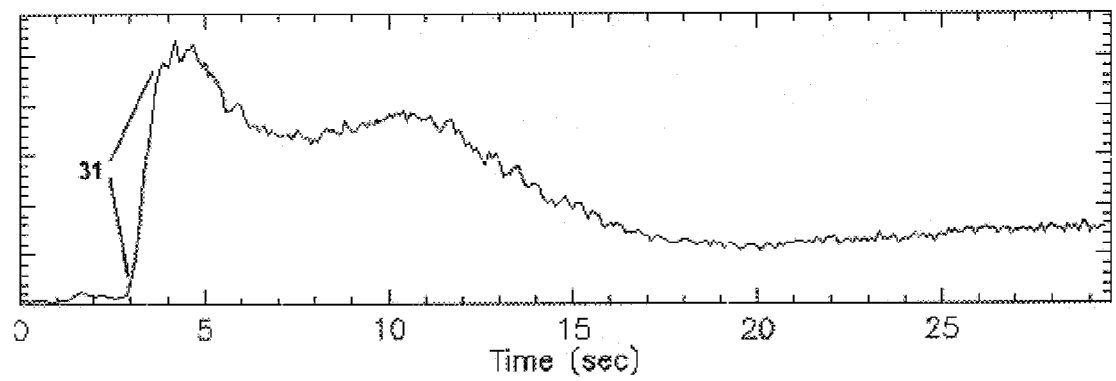
FIG. 4 is an activity versus time array of acquired data for an imaging field of view.
Figure 5:
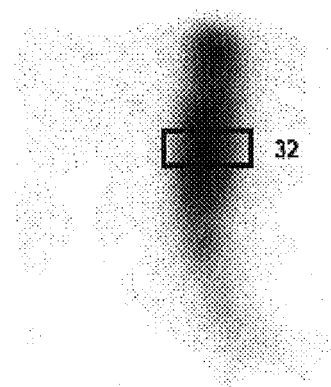
FIG. 5 is an image of the bolus of radiotracer entering the cardiac system and a region of interest corresponding to the superior vena cava.

In the current embodiment, the injected bolus is located as it first appears within the acquired field of view and tracked as it traverses the circulatory system to the heart. As an example, an activity versus time array is generated automatically from the full field of view, as shown in FIG. 4, with the activity expressed in events per second represented by the Y axis and the time in seconds relative to the start of the acquisition represented by the X axis. This time activity curve is analyzed to determine the time interval of entry of the bolus within the field of view. The time interval is identified by the characteristic rise in activity when the bolus enters the field of view 31, as determined by the level of the first derivative of the data. At a defined and variable time period after the bolus enters the field of view, a representative image is presented and a region of interest 32, as shown in the example of FIG. 5, is automatically placed to delineate the superior vena cava (SVC). The automated placement of the region of interest location is determined, for example, by a weighted center of mass calculation for the accumulated activity.

Figure 6:
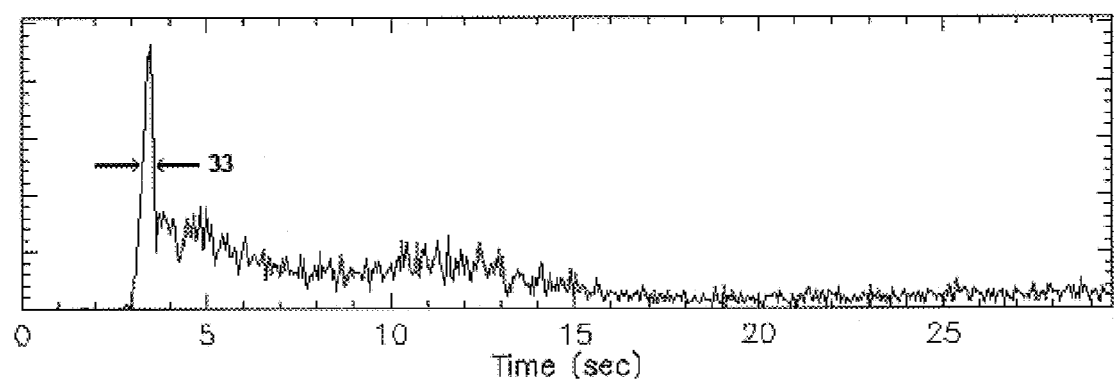
FIG. 6 is an activity versus time array of acquired data for the region of interest shown in FIG. 5.

FIG. 6 shows an activity versus time array for an example of the current embodiment, with the activity expressed in events per second represented by the Y axis and the time in seconds relative to the start of the acquisition represented by the X axis, generated from the defined region of interest and displayed. Using this data, the bolus is analyzed for compactness, for example, by determining the full width half maximum (FWHM) 33 of the filtered curve. If the bolus FWHM quality measurements exceed specified and variable minimums, typically 1.5 seconds, for example, processing is stopped and a message is displayed to the operator stating the measured FWHM and the defined limits. The bolus width may be excessive due to, but not limited to, injection technique, injection site, or physiology of the patient.

The operator may choose to adjust the region, continue processing, or dismiss the processing. The operator may choose to adjust the region of interest defining the SVC when the automatic position determination has resulted in interference from other circulatory structures. If the operator has made changes to the region of interest, the SVC analysis is repeated. If the operator chooses to continue processing of the acquired data, subsequent displays may include notification of the SVC quality control exceeding the defined limits.

The SVC quality control data is further analyzed in the current embodiment to detect any fragmentation of the bolus. To detect fragmentation of the bolus, a value equal to one half the highest detected event is used as a threshold value for the current embodiment. The data is scanned for discontinuous series exceeding the threshold value. Each discontinuous series of data represents a fragmentation of the bolus, possibly due to, but not limited to, injection technique, injection site, or physiology. The operator may choose to adjust the region of interest defining the SVC when the automatic position determination has resulted in interference from other circulatory structures. If the operator has made changes to the region of interest, the SVC analysis is repeated. If the operator chooses to continue processing of the acquired data, subsequent displays may include notification of the SVC quality control exceeding the defined limits.

Figure 7:
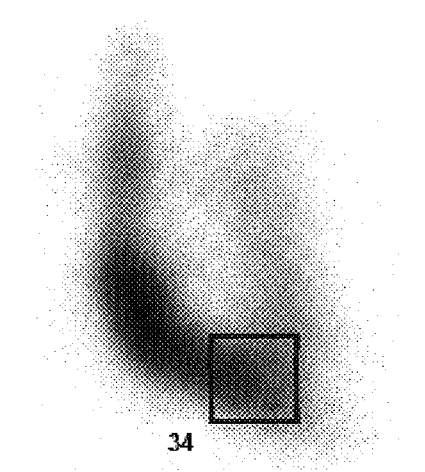
FIG. 7 is an image of the bolus of radiotracer passing through the cardiac system and a region of interest corresponding to the right ventricle of the heart.

In using the current embodiment utilized for a cardiopulmonary analysis, after localization of the SVC and continued processing, the bolus transit is tracked to the right ventricle (RV) of the heart. As shown in the example of FIG. 7, a RV region of interest 34 is generated within the RV. The RV is isolated by its temporal and spatial relationship to the SVC. The bolus transits the RV at a time interval after the SVC transit, and the RV location is below the SVC. Once the bolus has reached the RV, there is a static period and reversal in the direction of flow for the bolus as it traverses from the right atrium through the RV to the pulmonary system.

Figure 8:
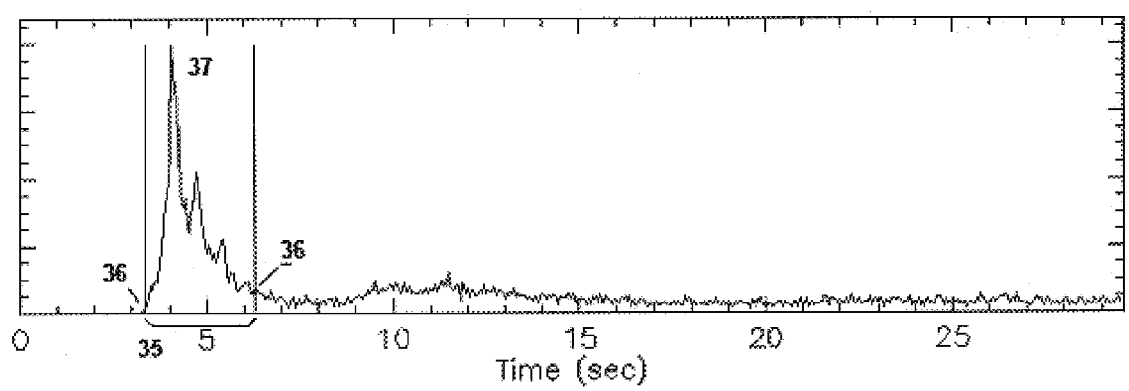
FIG. 8 is an activity versus time array of acquired data for the region of interest shown in FIG. 7.

FIG. 8 shows an activity versus time array for the example, with the activity expressed in events per second represented by the Y axis and the time in seconds relative to the start of the acquisition represented by the X axis, generated from the RV region of interest 34. This activity versus time array is used to derive a bracketed RV time interval 35 for further RV analysis. The RV time interval 35 is defined by a defined and changeable relative level of activity 36 prior to and after the peak activity time interval 37.

Figure 9:
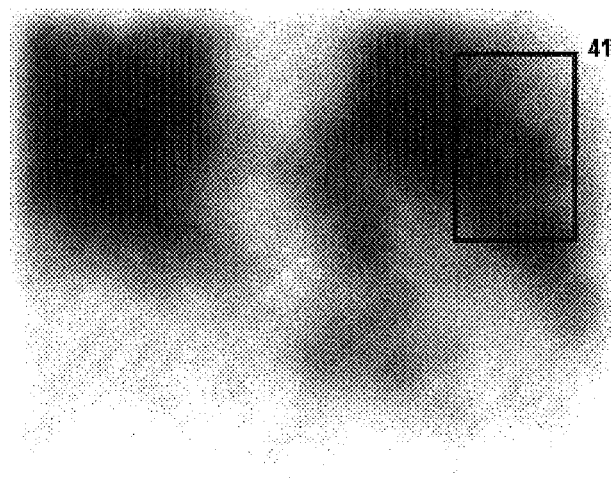
FIG. 9 is an image of the bolus of radiotracer passing through the pulmonary system and a region of interest corresponding to the lungs.
Figure 10:
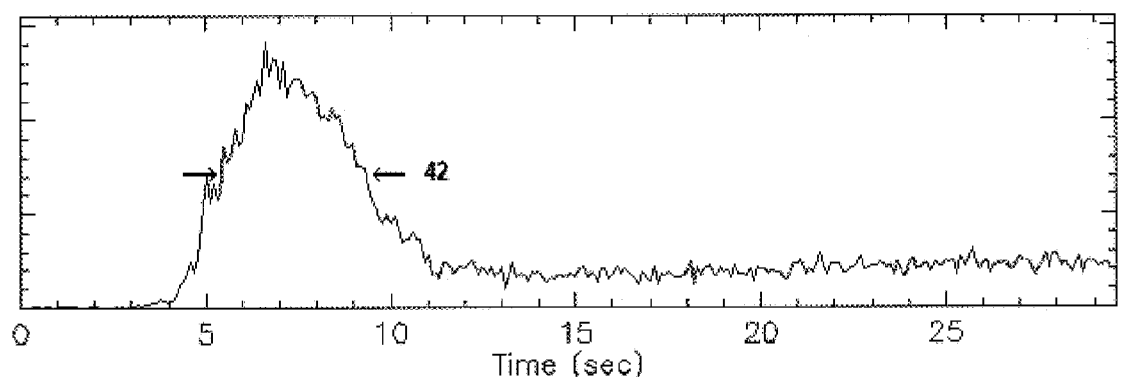
FIG. 10 is an activity versus time array of acquired data for the region of interest shown in FIG. 9.

Continuing with the cardiopulmonary example, after identification of the RV location and RV time interval 35, the activity distribution of the bolus through the pulmonary system is followed and a pulmonary region of interest 41 is selected for further transit analysis, as shown in FIG. 9. The pulmonary region of interest selected to maximize the inclusion of the left lung and limited to avoid overlapping the inflow to the SVC, the RV, or outflow to the LV. The region may be defined through thresholding and masking to encompass the full lung field, or may be a limited region 41. This region of interest is used to define the temporal interval of the pulmonary transit (pulmonary transit interval 42). All data within the pulmonary transit interval 42 is considered as lung and may be used for later background, and crosstalk, correction during the left ventricle processing to adjust the activity baseline and provide accurate functional measurement. FIG. 10 shows an activity versus time array generated from the pulmonary region of interest 41, with the activity expressed in events per second represented by the Y axis and the time in seconds relative to the start of the acquisition represented by the X axis. The full width half maximum, for example, may be used as a measure of the pulmonary transit interval 42.

Figure 11:
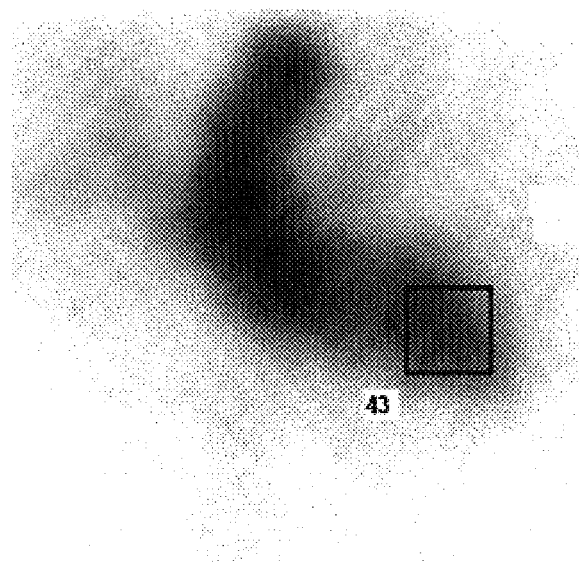
FIG. 11 is an image of the bolus of radiotracer passing through the cardiac system and a region of interest corresponding to the left ventricle of the heart.
Figure 12:
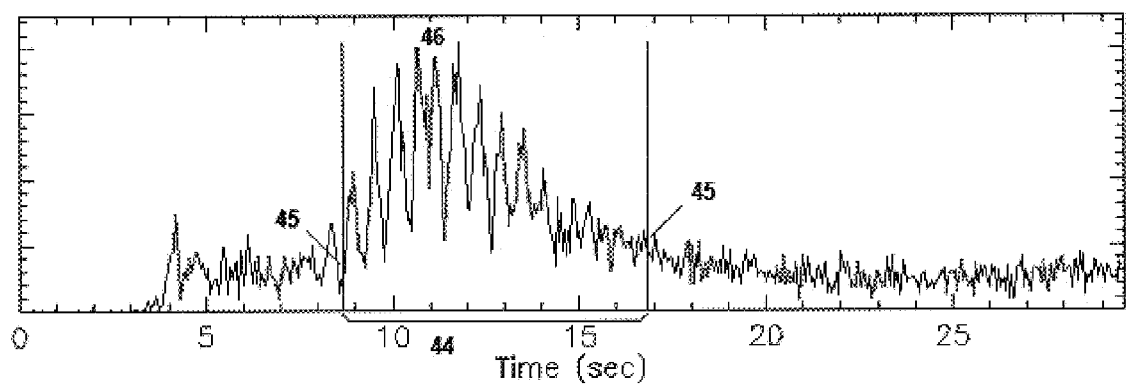
FIG. 12 is an activity versus time array of acquired data for the region of interest shown in FIG. 11.

After identification of the pulmonary region of interest 41 (FIG. 9) and pulmonary transit time interval 42 (FIG. 10), the bolus transit through the left ventricle (LV) is isolated in time after the lung transit interval. As shown in FIG. 11, a LV region of interest 43 is generated within the LV, preferably with minimal intrusion of other structures such as the RV and lung, to avoid inclusion of event data not associated with the LV. The LV is identified by its temporal relationship to the pulmonary transit interval and the LV spatial relationship to the RV in conjunction with the focal activity distribution. FIG. 12 shows an activity versus time array, with the activity expressed in events per second represented by the Y axis and the time in seconds relative to the start of the acquisition represented by the X axis, for the LV region of interest 43. This activity versus time array is used to derive a bracketed LV time interval 44 for further LV analysis. The LV time interval 44 is defined by a changeable relative level of activity 45 prior to and after the peak activity time interval 46. In the current embodiment, the LV interval is defined by the 25 percent of maximum points prior to and after the peak. In the case of a large background contribution, the starting time selection is limited to being no earlier than the lung maximum. The end time is limited to being no later than the LV peak plus 10 seconds.

Additional regions may be identified and processed automatically as appropriate during processing to provide additional quantitative and qualitative analysis. For example, these regions may include the pulmonary artery and aorta. The processing sequence is described as a linear progression but, where appropriate, the processing and analysis of the data may occur in parallel with other operations. It is logical to assume that this could and will be extended, but is not limited, to perform other qualitative and quantitative processing, including automatic shunt determination and quantification, volume and cardiac output, regional wall motion and ejection fraction analysis, and phase quantification.

Quantitative Processing

Figure 13:
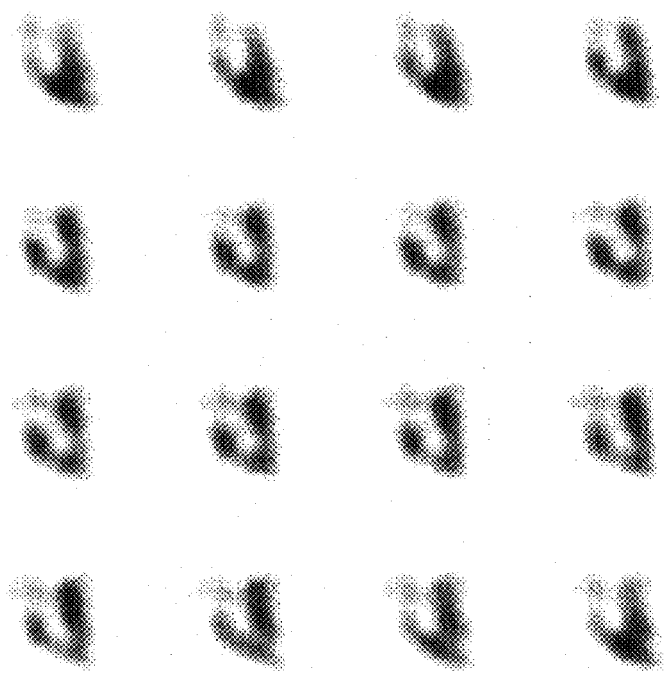
FIG. 13 shows a representative right ventricle cycle.
Figure 14:
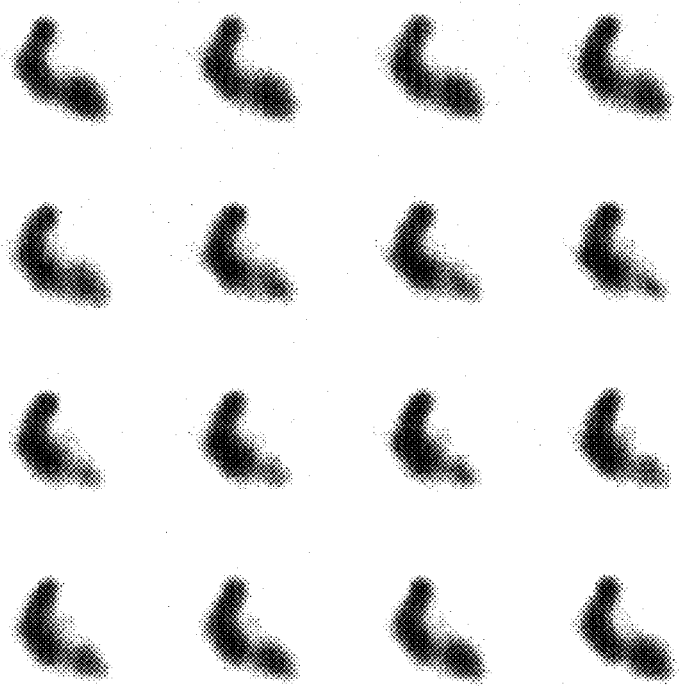
FIG. 14 shows a representative left ventricle cycle.

Continuing with the cardiopulmonary example, at the conclusion of the quality control analysis with the initial regions of interest defined and the bolus quality within limits, or operator selection to continue, the automatic analysis may continue with identification and creation of a representative RV cycle as shown in FIG. 13 and a representative LV cycle as shown in FIG. 14 from one or more cardiac cycles occurring during bolus transit of the RV and LV respectively. The number of images created per representative cycle is a defined and changeable value and is selected to provide adequate data density and temporal resolution for analysis, display, and review. Typically, the representative cycle is created as 16 frames of data when processing using high temporal resolution during acquisition (1 ms), and may be represented by as few as 8 frames when using lower temporal resolutions. As the definition and processing of the data is substantially similar for both ventricles, the process will be described in general terms applicable to both ventricles. Where there is a significant difference in the processing sequence, this will be pointed out.

Figure 15:
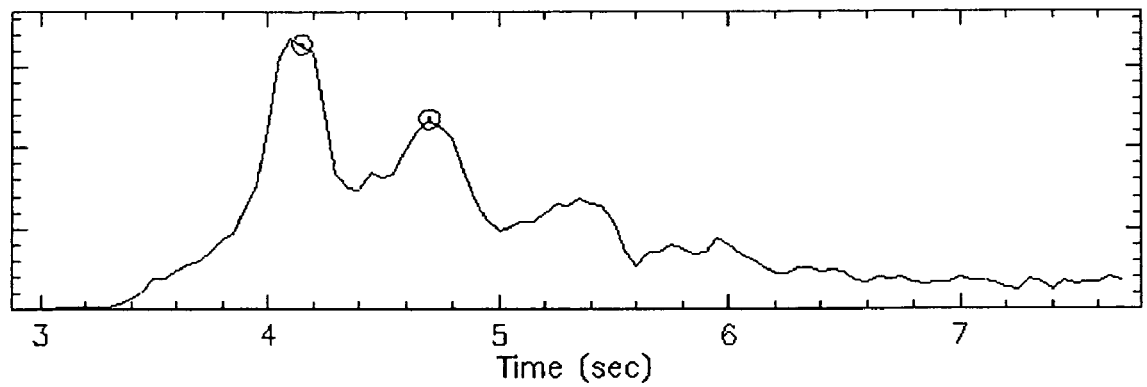
FIG. 15 is a partial activity versus time array of acquired data for a ventricle cycle.
Figure 16:
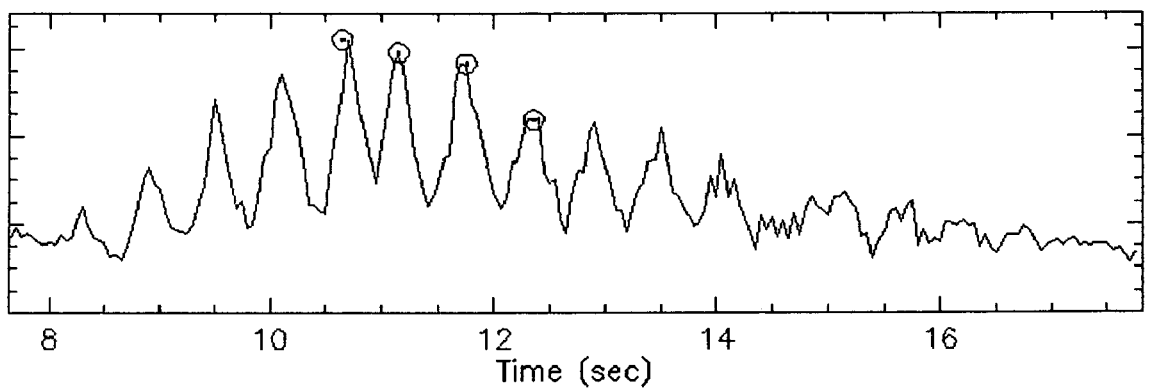
FIG. 16 is a partial activity versus time array of acquired data for a ventricle cycle.
Figure 17:
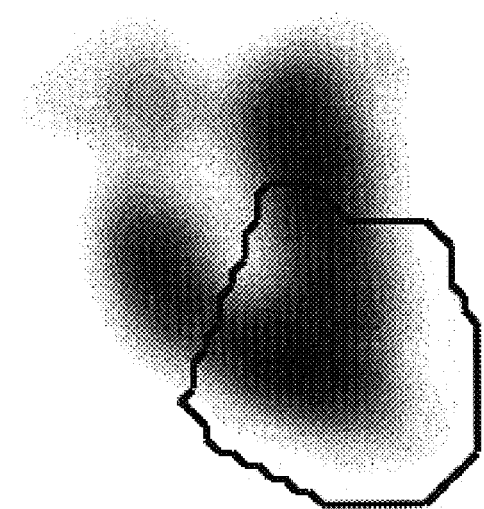
FIG. 17 shows a right ventricle with a defined new region outlined.
Figure 18:
FIG. 18 shows a left ventricle cycle with a defined new region outlined.

The RV time interval 35 and LV time interval 44 (see FIG. 8, 12) defined during the quality control processing of the ventricle is analyzed to create a representative ventricle cycle. As shown in FIGS. 15 and 16, the end diastolic time for all cycles within the interval is identified and subdivided into a number of equal intervals. The data from the equivalent intervals of each end diastolic to end diastolic period is accumulated into separate arrays to build a single initial representative cycle. The first harmonic Fourier analysis as described by the following equation:

$$A \cdot \cos(2\pi t/T) + P$$

is performed on the initial representative cycle to derive a phase and amplitude representation of the cycle. A center of mass calculation is performed for the area located by the ventricle quality control region of interest. The identified center point is used to perform an outward radial search in 5 degree increments on the cycle, phase and amplitude data to locate the ventricle valve and wall boundaries. The boundaries are used to define a new region encompassing the full ventricle, as shown in FIGS. 17 (RV) and 18 (LV). This region is representative of the end diastolic blood pool for the ventricle. The new region is used to generate a refined and encompassing time activity curve that is reanalyzed to determine a set of new end diastolic times. Of the identified end diastolic points, or maximum events per cardiac cycle, a representative set after and inclusive of the peak end diastolic interval based on a defined and changeable threshold is determined. The defined points for creating a representative cycle are chosen to include the peak and events after the peak. For the RV, a maximum of three ED peaks are selected, to allow for adequate mixing of the bolus within the ventricle blood pool while avoiding background contribution from the lung. For the LV, a maximum of 5 ED peaks are selected, to minimize background contribution from lung. More peaks are allowed for the LV selection because of the increased bolus transit time within LV due to the passage through the pulmonary circulation. As an equivalent alternative, the points of maximal downslope may be substituted for the ED peaks for creating the representative cycle.

A final representative cycle for the ventricle is created in the same manner as previously with the newly defined points. After creation of the new representative cycle, the same techniques as described previously may be applied to iteratively refine the region of interest for the ventricle. The refinement of the ventricle region of interest is stopped after three iterations or a change of under one percent in the area of the region.

Figure 19:
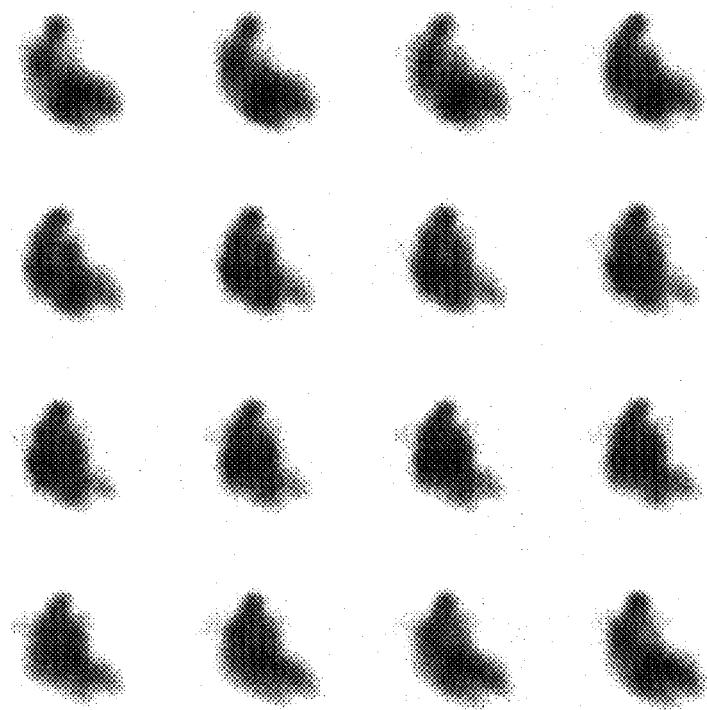
FIG. 19 shows a first combined representative composite right and left ventricle cycles.
Figure 20:
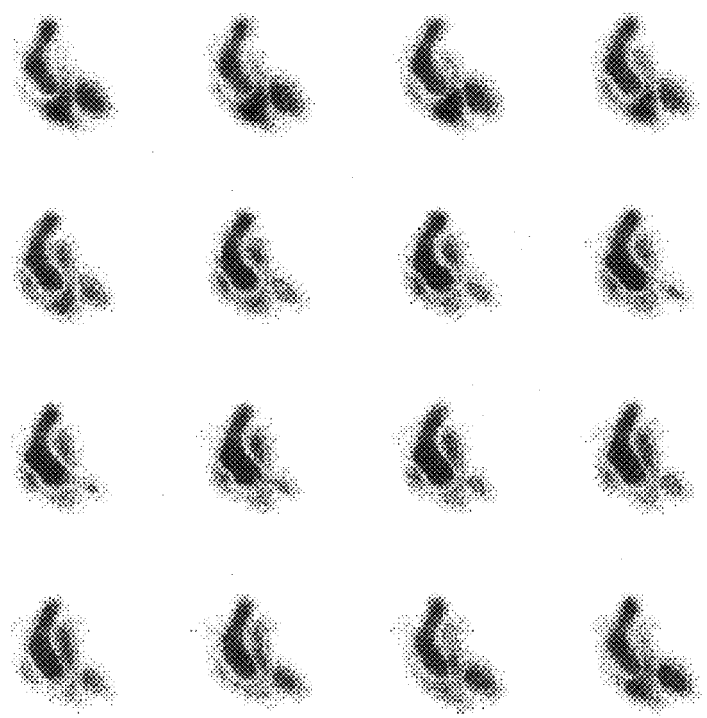
FIG. 20 shows a second combined representative composite right and left ventricle cycles.

When a final region of interest for a ventricle is defined, further quantitative and qualitative analyses may be performed to obtain, for example, ventricular ejection fractions, volumes, and cardiac outputs, along with wall motion and other functional results, such as, but not limited to, phase histogram and contractility analysis. The representative composite ventricle cycles may be combined to give, for example, a bloodpool gated cycle equivalent image (first combined representative composite right and left ventricle cycles, shown in FIG. 19) and a RV/LV color-coded overlay image for comparative visualization (second combined representative composite right and left ventricle cycles, shown in FIG. 20).

When processing is complete, the results of the automated processing may be automatically collated and recorded for immediate and later review on the same or a different system.

Note that the method and apparatus described above could be used, as disclosed or in a modified fashion, for other analyses beyond those listed in the cardiopulmonary example. Organs/systems such as the liver, digestive system, brain, etc. might be analyzed, for example. In addition, the method of the invention can also be applied to technologies other than nuclear medicine that use the transit of a bolus for evaluation—such as magnetic resonance imaging (MRI) and computed tomography (CT), for example. Furthermore, because the composite cardiac cycle images generated are equivalent to a gated cardiac equilibrium pool study, these same methods may be applied in that case as well.

The computer program listing source code of the appendix is of a software module for implementing a portion of the processing described above for a preferred embodiment, but this module does not contain, for example, necessary user interface functionality. Text, image, and other data outputs are displayed on one or more graphical monitors. Input from the user may come from a keyboard and mouse or other input devices as appropriate to the task. The graphical user interface may be implemented using a custom display system or may, as an example, be provided by a Windows or X/Motif based computer system. The graphical user interface provides, but is not limited to, display, manipulation, and analysis, of regions of interest, curves, and images.

The invention has been described hereinabove using specific examples; however, it will be understood by those skilled in the art that various alternatives may be used and equivalents may be substituted for components or steps described herein, or the order of steps may be changed, or substitutes for the described components provided, without deviating from the scope of the invention. Modifications may be necessary to adapt the invention to a particular situation or to particular needs without departing from the scope of the invention. It is intended that the invention not be limited to the particular implementation described herein, but that the claims be given their broadest interpretation to cover all embodiments, literal or equivalent, covered thereby.

What is claimed is:

1. A method of processing patient data using a radiation detector and a computer, said method comprising the steps of:
   using said radiation detector to acquire image data representing an image, said acquiring performed for some period of time using the radiation detector;
   using the computer for automatically detecting and isolating a feature portion of the image;
   identifying at least one region of interest of the image based on said feature portion;
   generating an activity versus time array corresponding to the at least one region of interest from said image data; and
   analyzing the activity versus time array for generating an output for use by a user, wherein said output represents a quality of a bolus of an injected radiotracer through the central circulatory system of the patient, and wherein said quality of the bolus includes one or both of compactness or fragmentation of the bolus.

2. The method of claim 1, wherein said feature is the superior vena cava of the patient.

3. The method of claim 2, wherein said identifying a region of interest step is first automatically performed by the computer.

4. The method of claim 3, wherein an operator of the radiation detector can subsequently adjust the region of interest after it has been first automatically identified by the computer.

5. The method of claim 4, wherein said analyzing the activity versus time array step is automatically performed by the computer.

6. The method of claim 5, wherein said detecting and isolating a feature portion step includes the steps of detecting one or both of a right and a left ventricle of the patient, wherein said at least one region of interest includes a region of interest in said one or both of said right and said left ventricle, and wherein said analysis step includes determining a traversal time of said bolus through said one or both of the right and the left ventricle.

7. The method of claim 6, wherein said detecting and isolating a feature portion step includes the step of detecting a lung of the patient, wherein said at least one region of interest includes a region of interest in the lung, and wherein said analysis includes determining a traversal time of said bolus through said lung.

8. The method of claim 7, wherein said analyzing the activity versus time array step includes the steps of:
   determining one or both of right ventricular cycle end points and left ventricular cycle endpoints;
   using said endpoints to create a respective representative cycle for one or both of said right ventricular cycle and said left ventricular cycle;
   analyzing said representative cycle to create a respective one or both of a comprehensive right ventricle and left ventricle region; and
   using said one or both of a comprehensive right ventricle and left ventricle region for one or both of:
      creating a respective one or both a right ventricular refined comprehensive cycle and a left ventricular refined comprehensive cycle, and
      making respective quantitative values measurements/qualitative outputs for one or both right ventricular and left ventricular measurements using original list data or the respective representative cycle.

9. The method of claim 8, wherein said quantitative measurements include one or more of:
   superior vena cava full width half maximum;
   pulmonary transit time;
   ventricular ejection fraction;
   ventricular volumes;
   stroke volume;
   cardiac output; and
   regurgitant fraction/shunt analysis,
and wherein said qualitative outputs include one or more of:
   a phase and amplitude display;
   a wall motion display;
   a gated equivalent composite right ventricle/left ventricle representative cycle; and
   a bi-color right ventricle/left ventricle representative cycle.

10. The method of claim 1, wherein said analyzing the activity versus time array step is automatically performed by the computer.

11. The method of claim 10, wherein said analyzing the activity versus time array step includes the steps of:
   determining one or both of right ventricular cycle end points and left ventricular cycle endpoints;
   using said endpoints to create a respective representative cycle for one or both of said right ventricular cycle and said left ventricular cycle;
   analyzing said representative cycle to create a respective one or both of a comprehensive right ventricle and left ventricle region; and
   using said one or both of a comprehensive right ventricle and left ventricle region for one or both of:
      creating a respective one or both a right ventricular refined comprehensive cycle and a left ventricular refined comprehensive cycle, and
      making respective quantitative values measurements/ qualitative outputs for one or both right ventricular and left ventricular measurements using original list data or the respective representative cycle.

12. The method of claim 11, wherein said quantitative measurements include one or more of:
   superior vena cava full width half maximum;
   pulmonary transit time;
   ventricular ejection fraction;
   ventricular volumes;
   stroke volume;
   cardiac output; and
   regurgitant fraction/shunt analysis,
and wherein said qualitative outputs include one or more of:
   a phase and amplitude display;
   a wall motion display;
   a gated equivalent composite right ventricle/left ventricle representative cycle; and
   a bi-color right ventricle/left ventricle representative cycle.

13. The method of claim 1, wherein
   said automatically identifying step includes the step of performing a weighted center of mass calculation on said image data, and further wherein
   said analyzing for compactness or fragmentation step includes the step of performing a full width half maximum calculation on said array.

14. A method of processing patient data using a radiation detector and a computer, said method comprising the steps of:
   using said radiation detector to acquire image data representing an image of a bolus of an injected radiotracer through the patient, said acquiring performed for some period of time using the radiation detector;
   detecting and isolating a feature portion of the image;
   using the computer for automatically identifying at least one region of interest of the image based on said feature portion;
   generating an activity versus time array corresponding to the at least one region of interest from said image data; and
   analyzing the activity versus time array for generating an output for use by a user, wherein said output represents a quality of the bolus including one or both of compactness or fragmentation of the bolus.

15. The method of claim 14, wherein said feature is the superior vena cava of the patient.

16. The method of claim 15, wherein said step of detecting and isolating a feature portion of the image is automatically performed by the computer.

17. The method of claim 16, wherein said detecting and isolating a feature portion step includes the step of detecting one or both of a right and a left ventricle of the patient, wherein said identifying at least one region of interest includes a region of interest in said one or both of said right and said left ventricle, and wherein said analysis includes determining a traversal time of said bolus through said one or both of the right and the left ventricle.

18. The method of claim 17, wherein said detecting and isolating a feature portion step includes the step of detecting a lung of the patient, wherein said at least one region of interest includes a region of interest in the lung, and wherein said analysis includes determining a traversal time of said bolus through said lung.

19. A method of processing patient data using a radiation detector and a computer, said method comprising the steps of:
   using said radiation detector to acquire image data representing an image of a bolus of an injected radiotracer through the central circulatory system of a patient, said acquiring performed for some period of time using the radiation detector;
   detecting and isolating a feature portion of the image;
   identifying at least one region of interest of the image based on said feature portion;
   generating an activity versus time array corresponding to the at least one region of interest from said image data to determine a compactness or fragmentation of the bolus; and
   using the computer for automatically analyzing the activity versus time array for generating an output for use by a user.

20. The method of claim 19, wherein said automatically analyzing the activity versus time array step includes the steps of:
   determining one or both of right ventricular cycle end points and left ventricular cycle endpoints;
   using said endpoints to create a respective representative cycle for one or both of said right ventricular cycle and said left ventricular cycle;
   analyzing said representative cycle to create a respective one or both of a comprehensive right ventricle and left ventricle region; and
   using said one or both of a comprehensive right ventricle and left ventricle region for one or both of:
      creating a respective one or both a right ventricular refined comprehensive cycle and a left ventricular refined comprehensive cycle, and
      making respective quantitative values measurements/ qualitative outputs for one or both right ventricular and left ventricular measurements using original list data or the respective representative cycle.

21. The method of claim 20, wherein said quantitative measurements include one or more of:
   superior vena cava full width half maximum;
   pulmonary transit time;
   ventricular ejection fraction;
   ventricular volumes;
   stroke volume;
   cardiac output; and
   regurgitant fraction/shunt analysis,
and wherein said qualitative outputs include one or more of:
   a phase and amplitude display;
   a wall motion display;
   a gated equivalent composite right ventricle/left ventricle representative cycle; and
   a bi-color right ventricle/left ventricle representative cycle.

22. A method of processing patient data using a radiation detector and a computer, said method comprising the steps of:
   using said radiation detector to acquire image data representing an image of a bolus of an injected radiotracer, said acquiring performed for some period of time using the radiation detector;
   using the computer for automatically detecting and isolating a feature portion of the image;
   using the computer for automatically identifying at least one region of interest of the image based on said feature portion;
   generating an activity versus time array corresponding to the at least one region of interest from said image data; and
   using the computer for automatically analyzing the activity versus time array to determine a quality of the bolus by determining one or both of compactness or fragmentation.

23. The method of claim 22, wherein said automatically identifying step includes the step of performing a weighted center of mass calculation on said image data.

24. The method of claim 22, wherein said analyzing for compactness or fragmentation step includes the step of performing a full width half maximum calculation on said array.

25. A system for acquiring and processing patient data, comprising:
   a radiation detector for acquiring image data representing an image from of an injected radiotracer from a patient for some period of time;
   a computer comprising:
      a storage medium for storing said image data;
      a processor; and
      a program memory for storing one or more programs for executing on said processor for performing the steps of:
         identifying a region of interest of an image represented by said image data,
         detecting and isolating a feature portion of the image,
         identifying at least one region of interest of the image based on said feature portion,
         generating an activity versus time array corresponding to the at least one region of interest from said image data, and
         analyzing the activity versus time array for compactness or fragmentation, and
   an output device for outputting a result of said analyzing.

* * * * *

UNITED STATES PATENT AND TRADEMARK OFFICE
CERTIFICATE OF CORRECTION

| | | |
|---|---|---|
| PATENT NO. | : 7,502,500 B2 | Page 1 of 1 |
| APPLICATION NO. | : 11/241686 | |
| DATED | : March 10, 2009 | |
| INVENTOR(S) | : William G. Greathouse | |

It is certified that error appears in the above-identified patent and that said Letters Patent is hereby corrected as shown below:

Column 1, line 15, please replace "patent" with "Patent"

Signed and Sealed this

Nineteenth Day of May, 2009

JOHN DOLL
*Acting Director of the United States Patent and Trademark Office*